United States Patent [19]

Steigerwald

[11] Patent Number: 4,490,144
[45] Date of Patent: Dec. 25, 1984

[54] URINE DRAINAGE RECEPTACLE WITH A NORMALLY OPEN REFLUX VALVE

[75] Inventor: Carl J. Steigerwald, Wauconda, Ill.

[73] Assignee: The Kendall Company, Boston, Mass.

[21] Appl. No.: 465,384

[22] Filed: Feb. 10, 1983

[51] Int. Cl.$^3$ .............................................. A61F 5/44
[52] U.S. Cl. .................................. 604/323; 604/335; 604/350
[58] Field of Search ....................... 137/533.17, 533.21, 137/533.29, 533.31, 38, 517, 854; 128/760, 762, 766, 767, 205.17; 604/317, 322–326, 335, 350

[56] References Cited

U.S. PATENT DOCUMENTS

| | | | |
|---|---|---|---|
| 882,831 | 3/1908 | Matthes et al. | 137/533.31 |
| 3,066,696 | 12/1962 | Hansley | 137/855 |
| 3,529,599 | 9/1970 | Folkman | 604/323 |
| 4,334,537 | 6/1982 | Peterson | 604/323 |

FOREIGN PATENT DOCUMENTS 1450599  4/1969  Fed. Rep. of Germany ...................... 137/533.31

Primary Examiner—C. Fred Rosenbaum
Assistant Examiner—J. L. Kruter
Attorney, Agent, or Firm—Powell L. Sprunger

[57] ABSTRACT

A liquid drainage system comprising, a receptacle having a chamber to receive liquid, a depending annular wall defining a valve seat at a lower portion thereof and an opening in the region of the seat, and a retainer assembly extending across the opening and having an aperture extending therethrough in the opening. The system has a valve element of elastic material comprising a disc being sufficiently large to extend across the opening and sealingly engage against the seat peripherally around the wall. The valve element has a stem extending from the disc and being slidably received in the aperture. The stem has a boss spaced from the disc with dimensions larger than the aperture such that the boss maintains the stem in the aperture. The stem has a sufficient length between the boss and disc such that the disc is spaced from the seat when the boss engages against the retainer assembly.

12 Claims, 4 Drawing Figures

URINE DRAINAGE RECEPTACLE WITH A NORMALLY OPEN REFLUX VALVE

BACKGROUND OF THE INVENTION

The present invention relates to liquid drainage systems, and more particularly to urine drainage systems.

Urine drainage systems, such as urine meters, have been proposed in the past. Such systems may comprise a receptacle having a chamber, a container having a cavity, a catheter, and a drainage tube communicating between the catheter and receptacle. The catheter is passed through the urethra of a patient until a drainage eye in a distal portion of the catheter is located in the patient's bladder. During use, urine drains from the bladder through the drainage eye, the catheter, and drainage tube into the receptacle where the urine output is collected and measured.

In one form, the system may have a conduit communicating between an upper portion of the chamber and an upper portion of the cavity. When it is desirable to empty urine from the receptacle, such as when it is full, the receptacle is tilted, and the urine passes from the chamber through the conduit into the cavity for retention therein. Normally, the receptacle would be provided with a vent in an upper portion of the receptacle having a bacteria filter in order to facilitate the emptying procedure from the receptacle into the container. However, it is desirable to prevent contact of the filter by the urine when the receptacle is being emptied, since such contact may render the filter inoperable. Also, it is desirable to prevent the reflux of urine into the drainage tube, since such refluxing urine may contain bacteria which may by retrograde movement pass from the drainage tube into the bladder with possible deleterious results to the patient.

SUMMARY OF THE INVENTION

A principal feature of the present invention is the provision of an improved liquid drainage system of simplified construction.

The liquid drainage system of the present invention comprises a receptacle having a chamber to receive liquid, a depending annular wall defining a valve seat at a lower portion thereof and an opening in the region of the seat, and a retainer assembly extending across the opening and having an aperture extending therethrough in the opening. The system has a valve element of elastic material comprising a disc being sufficiently large to extend across said opening and sealingly engage against the seat peripherally around the wall. The valve element has a stem extending from the disc and being slidably received in the aperture, with the stem having a boss spaced from the disc with dimensions larger than the aperture such that the boss maintains the stem in the aperture. The stem has a sufficient length between the boss and disc such that the disc is spaced from the seat when the boss engages against the retainer assembly.

A feature of the present invention is that the valve element is in an open position spaced from the seat when the receptacle is placed in an upright position.

Thus, a feature of the present invention is that the valve element automatically permits passage of urine past the seat when the receptacle is placed in an upright position.

Still another feature of the invention is that the valve element automatically closes against the seat when the receptacle is placed in an inverted position.

Yet another feature of the invention is that the valve element closes when refluxing urine in the receptacle chamber strikes the valve element Thus, a feature of the present invention is that the valve element is closed against the seat when the receptacle is tilted in order to pour liquid from the receptacle chamber.

Further features will become more fully apparent in the following description of the embodiments of this invention and from the appended claims

DESCRIPTION OF THE PREFERRED EMBODIMENTS

Figure 1:
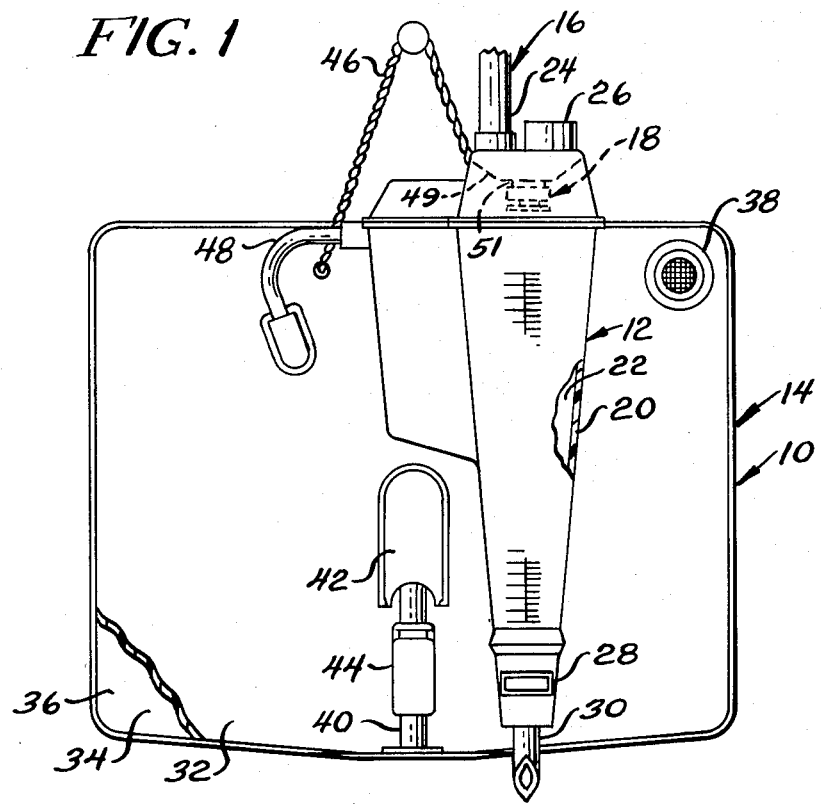
FIG. 1 is a fragmentary elevational view of a liquid drainage system of the present invention.

Referring now to FIG. 1, there is shown a liquid drainage system generally designated 10 comprising a receptacle 12, a container 14, a drainage tube 16, and a valve 18 in the receptacle 12. The receptacle 12 has a rigid outer wall 20, such as a suitable plastic material, defining a chamber 22 in the receptacle 12. As shown, a downstream end 24 of the drainage tube 16 communicates with an upper portion of the chamber 22 at a location above the valve 18. The receptacle 12 may have a vent 26 containing a bacteria filter of known type which communicates between the chamber 22 and the atmosphere in order to remove bacteria from the air passing through the vent 26 into the chamber 22. In a preferred form, as shown, the vent 26 is located above the valve 18. The receptacle 12 may also have a valve 28 of known type in order to empty urine from the chamber 22 through a tubular section 30, if it is desired to obtain a sample of the urine.

The container 14 has a front wall 32 of flexible plastic material, and a back wall 34 of flexible plastic material, with the front and back walls 32 and 34 being joined at their periphery in order to define a cavity 36 between the front and back walls 32 and 34. The container 14 may have a vent 38 having a bacteria filter of known type communicating between the cavity 36 and the atmosphere in order to remove bacteria from the air passing from the atmosphere into the cavity 36. The container 14 may have a lower tubular section 40 with an outer end received in a pocket 42 on the front wall 32 in a storage position of the tubular section 40. When it is desired to drain urine from the cavity 36, the tubular section 40 is removed from the pocket 42, and a clamp 44 of known type on the tubular section 40 is opened to permit passage of urine through the tubular section 40. After drainage of urine from the cavity 36, the clamp 44 is again closed, and the tubular section 40 is placed in the pocket 42 in the storage position of the tubular section 40. The container 14 may have a cord 46 secured to an upper portion of the container 14 in order to hang the receptacle 12 and container 14 from a suitable object, such as a bed rail, with an upper portion of the receptacle 12 being releasably retained on an upper portion of the container 14. As shown, the system 10 may have a flexible conduit 48 which communicates between an upper portion of the chamber 22 and an upper portion of the cavity 36 for a purpose which will be described below.

In use of the system 10, a catheter (not shown) is passed through the urethra of a patient until a drainage eye in a distal end of the catheter is located in the patient's bladder. In this configuration, a proximal end of the catheter located outside the patient's body is connected to an upstream portion of the drainage tube 16. Urine drains through the drainage eye, the catheter, and the drainage tube 16 into the receptacle 12 where the urine is collected and measured. When it is desired to empty urine from the receptacle 12, such as when it is full, the receptacle 12 is lifted from the container 14, and is placed in a tilted position such that the urine collects in an upper portion of the chamber 22 and passes from the chamber 22 through the conduit 48 into the container cavity 36 for retention therein. During this time, it is desirable to prevent the contact of urine against the bacteria filter in the vent 26, since such contacting urine may render the bacteria filter in the vent 26 inoperable. Also, it is desirable to prevent the reflux of urine from the receptacle chamber 22 into the drainage tube 16, since such refluxing urine may cause the passage of bacteria into the drainage tube 16 and by retrograde movement into the patient's bladder with possible deleterious results to the patient. Further, it is desirable to prevent the reflux of urine against the vent 26 and into the drainage tube 16 when the system 10 is mishandled, such as by turning the receptacle 12 into an inverted position. As will be seen below, the valve 18 in the receptacle 12 solves the problems associated with the prior liquid drainage systems.

Figure 2:
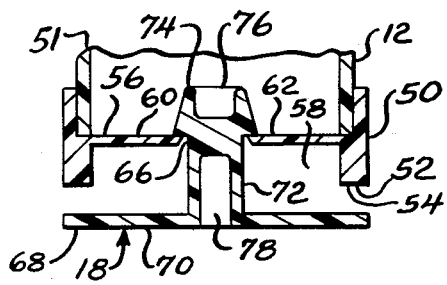
FIG. 2 is a fragmentary sectional view illustrating a valve element of the system in an open position.
Figure 3:
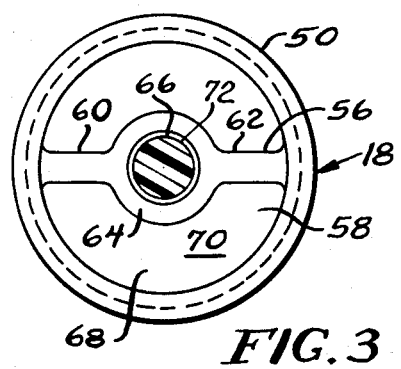
FIG. 3 is a sectional view showing the valve element of FIG. 2.

With reference to FIGS. 1-3, the receptacle 12 has a baffle 49 extending across an upper portion of the chamber 22 below the vent 26 and drainage tube 16 and a tubular section 51 depending from the baffle 49. The receptacle 12 has a depending annular wall 50 secured to the tubular section 51 with a lower edge 52 of the wall 50 defining a valve seat 54 at a lower portion of the wall 50. The receptacle 12 also has a retainer assembly 56 extending across an opening 58 defined by the wall 50. The retainer assembly 56 comprises a pair of arms 60 and 62 extending from opposed sides of the wall 50 across the opening 58, and a central ring 64 having a generally central aperture 66. As shown, the ring 64 is tapered around the aperture 66 for a purpose which will be described below.

The valve 18 has a valve element 68 of elastic material, such as rubber. The valve element 68 has a circular disc 70 which is sufficiently large to extend across the opening 58 and sealingly engage against the seat 54. The valve elenent 68 has a stem 72 extending upwardly from a central portion of the disc 70, with the stem 72 having a boss 74 at an outer end of the stem 72 and spaced from the disc 70, with the boss 74 having larger lateral dimensions than the aperture 66 in order to retain the stem 72 slidably received in the aperture 66. As shown, the boss 74 has an inner bore 76, and the stem 72 has a bore 78 in a lower portion of the stem 72 when the receptacle 12 is located in an upright position.

During assembly of the valve 18 onto the wall 50, the boss 74 is pushed through the aperture 66, with the tapered ring 64 and bores 76 and 78 facilitating the placement procedure, until the boss 74 is located above the retainer assembly 56. With reference to FIGS. 1 and 2, when the receptacle 12 is placed in an upright position, the boss 74 engages the retainer assembly 56, and the valve element 68 automatically assumes an open position with the disc 70 spaced from the seat 54. In this configuration, the stem 72 has a sufficient length between the boss 74 and disc 70 in order that the disc 70 is spaced from the seat 54 when the boss 74 engages the retainer assembly 56. Thus, in this configuration, the valve 18 permits passage of urine from the drainage tube 16 past the valve seat 54 into the chamber 22 at a location below the valve 18. During this time, the vent 26 facilitates passage of urine through the valve 18 when the receptacle 12 is located in an upright position.

Figure 4:
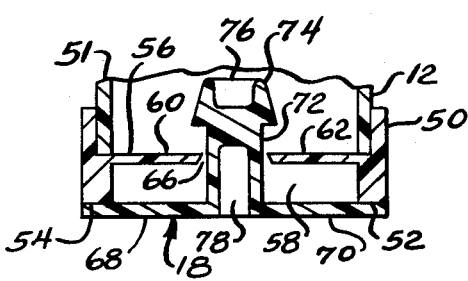
FIG. 4 is a fragmentary sectional view illustrating the valve element in a closed position against a seat.

With reference to FIGS. 1 and 4, when the receptacle is tilted or is placed in an inverted position, the disc 70 sealingly engages against the seat 54 to close the valve 18 due to the reflux of urine against the valve element 68 or to the weight of the valve element 68 caused by the action of gravity. Thus, the valve element 68 assumes its closed position against the seat 54 in order to prevent the reflux of urine against the bacteria filter in the vent 26, and prevent the reflux of urine into the drainage tube 16 which otherwise might render the filter inoperable, and cause possible retrograde migration of bacteria into the patient's bladder. When the receptacle is tilted in order to empty the chamber 22, the disc 70 is sufficiently flexible to vibrate and permit rapid passage of air from the vent 26 into a lower portion of the chamber 22 in order to replace the urine which passes from the chamber 22 during the emptying procedure. In accordance with the present invention, the valve 18 is very sensitive in moving between its open and closed positions in order to assure the flow of urine through the valve 18 and prevent the reflux of urine past the valve 18.

The foregoing detailed description is given for clearness of understanding only, and no unnecessary limitations should be understood therefrom, as modifications will be obvious to those skilled in the art.

I claim:

1. A urine drainage system, comprising:
    a receptacle having a chamber to receive liquid, a depending annular wall defining a valve seat at a lower portion thereof and an opening in the region of the seat, and a retainer assembly extending across said opening and having an aperture extending therethrough in said opening; and means to suspend the device in a vertical upright position and;
    a valve element means of elastic material comprising a disc member means being sufficiently large to extend across said opening and sealingly engage against said seat peripherally around the wall, and a stem extending from said disc member means and being slidably received in said aperture, said stem having a boss spaced from said disc member means with dimensions larger than said aperture such that the boss maintains the stem in the aperture, said stem having a sufficient length between the boss and disc such that the disc member means is spaced from the seat when the boss engages against the retainer assembly, said disc member means depending from the stem when the valve element means is in a normally open position when the receptacle is vertically suspended in an upright position.

2. The system of claim 1 wherein the retaining assembly comprises a pair of arms extending between opposed sides of the wall and a central ring defining said aperture.

3. The system of claim 1 wherein the retaining assembly is tapered around said aperture.

4. The system of claim 1 including a vent communicating between the atmosphere and the valve element means at a location above the valve element means when the receptacle is in an upright position.

5. The system of claim 1 including a bore in said boss.

6. The system of claim 1 including a bore in a lower portion of the stem when the receptacle is located in an upright position.

7. The system of claim 1 including a drainage tube communicating with the chamber at a location above the valve element means when the receptacle is located in an upright position.

8. The system of claim 1 including a container having a cavity.

9. The system of claim 8 including a conduit communicating between an upper portion of the chamber and an upper portion of the cavity.

10. The system of claim 1 wherein said disc member means is circular.

11. The system of claim 1 wherein said aperture is located generally centrally in said retainer assembly, and in which said stem is located generally centrally on said disc.

12. The system of claim 1 wherein the wall extends from a baffle located in an upper portion of the chamber.

* * * * *